(12) United States Patent
Van Zessen et al.

(10) Patent No.: US 9,944,961 B2
(45) Date of Patent: Apr. 17, 2018

(54) PROCESS FOR REMOVING SULPHIDE FROM AN AQUEOUS SOLUTION

(71) Applicant: Paques I.P. B.V., Balk (NL)

(72) Inventors: Erik Van Zessen, Heerenveen (NL); Antonius Johannes Jorna, Balk (NL); Sjoerd Hubertus Jozef Vellinga, Tjalleberd (NL); Hendrik Dijkman, IJlst (NL)

(73) Assignee: Paques I.P. B.V., Balk (NL)

( * ) Notice: Subject to any disclaimer, the term of this patent is extended or adjusted under 35 U.S.C. 154(b) by 0 days.

(21) Appl. No.: 15/024,485

(22) PCT Filed: Sep. 26, 2014

(86) PCT No.: PCT/NL2014/050660
§ 371 (c)(1),
(2) Date: Mar. 24, 2016

(87) PCT Pub. No.: WO2015/047091
PCT Pub. Date: Apr. 2, 2015

(65) Prior Publication Data
US 2016/0215310 A1     Jul. 28, 2016

(30) Foreign Application Priority Data

Sep. 26, 2013    (EP) ..................... 13186184

(51) Int. Cl.
| | | |
|---|---|---|
| *C12P 11/00* | (2006.01) | |
| *C01B 17/05* | (2006.01) | |
| *C01B 17/06* | (2006.01) | |
| *C02F 3/30* | (2006.01) | |
| *B01D 53/14* | (2006.01) | |
| *B01D 53/18* | (2006.01) | |
| *C02F 3/22* | (2006.01) | |
| *C02F 3/34* | (2006.01) | |
| *C02F 101/10* | (2006.01) | |

(52) U.S. Cl.
CPC .......... *C12P 11/00* (2013.01); *B01D 53/1425* (2013.01); *B01D 53/1493* (2013.01); *B01D 53/18* (2013.01); *C01B 17/05* (2013.01); *C01B 17/06* (2013.01); *C02F 3/301* (2013.01); *C02F 3/223* (2013.01); *C02F 3/345* (2013.01); *C02F 2101/101* (2013.01); *Y02W 10/15* (2015.05)

(58) Field of Classification Search
None
See application file for complete search history.

(56) References Cited

U.S. PATENT DOCUMENTS 5,041,216 A * 8/1991 Henzler ................. B01J 8/1818
                                                                                210/151
5,166,072 A     11/1992   Krauling et al.

FOREIGN PATENT DOCUMENTS

| EP | 0 997 183 A1 | 5/2000 |
|---|---|---|
| WO | WO-92/10270 A1 | 6/1992 |
| WO | WO-94/29227 A1 | 12/1994 |
| WO | WO-98/04503 A1 | 2/1998 |
| WO | WO-01/27042 A1 | 4/2001 |
| WO | WO-2013/079075 A1 | 6/2013 |

OTHER PUBLICATIONS

Soreanu et al., Removal of hydrogen sulfide from gas streams using biological processes, Candian Biosystems Engineering vol. 48 2006.*
International Search Report issued in International Patent Application No. PCT/NL2014/050660 dated Jul. 1, 2015.

* cited by examiner

*Primary Examiner* — Suzanne M Noakes
*Assistant Examiner* — Stephen M Chong
(74) *Attorney, Agent, or Firm* — Gilberto M. Villacorta; Sunit Talapatra; Foley & Lardner LLP

(57) ABSTRACT

A process for removing sulphide from an aqueous solution comprising sulphide is disclosed, in which the aqueous solution is subjected to sulphide-oxidizing bacteria in the presence of oxygen in a reactor to oxidize sulphide to elemental sulphur. According to the process, a molecular-oxygen containing gas is supplied to a reactor containing the sulphide-oxidizing bacteria in an aqueous medium, such that one or more aerated zones and one or more non-aerated zones are created in the aqueous medium with upward liquid flow in the aerated zones and downward liquid flow in the non-aerated zones; and a feed stream of the aqueous solution comprising sulphide is injected into the reactor in the one or more non-aerated zones, wherein the one or more aerated zone(s) are not separated from the one or more non-aerated zone(s) by means of vertically extending reactor internal.

17 Claims, 2 Drawing Sheets

PROCESS FOR REMOVING SULPHIDE FROM AN AQUEOUS SOLUTION

CROSS-REFERENCE TO RELATED APPLICATIONS

This application is the National Phase of International Patent Application No. PCT/NL2014/050660, filed Sep. 26, 2014, published on Apr. 2, 2015 as WO 2015/047091 A1, which claims priority to European Patent Application No. 13186184.1, filed Sep. 26, 2013. The contents of these applications are herein incorporated by reference in their entirety.

FIELD OF THE INVENTION

The invention relates to a process for removing sulphide from an aqueous solution comprising sulphide, wherein the aqueous solution is subjected to sulphide-oxidising bacteria in the presence of oxygen in a reactor to oxidise sulphide to elemental sulphur.

BACKGROUND OF THE INVENTION

It is well-known to remove sulphur compounds such as hydrogen sulphide, sulphur oxides, carbon disulphide and lower alkyl mercaptans from gaseous flows by means of scrubbing the gaseous stream in an absorption tower with an aqueous washing solution, such as for example a solution of sodium or potassium carbonate. Thus, a purified gaseous stream and a washing solution loaded with sulphide is obtained, optionally after reduction of dissolved sulphur oxides into sulphide.

In WO92/10270 a process is disclosed wherein an aqueous solution containing sulphide obtained from scrubbing a sulphur-containing gaseous effluent is subjected to sulphur-oxidising bacteria in the presence of oxygen in a reactor to oxidise the sulphide to elemental sulphur and hydroxide.

In WO94/29227 a process is disclosed for oxidation of sulphide to elemental sulphur with sulphide-oxidising bacteria in an airlift loop reactor wherein a vertical circulation is maintained by means of an oxygen-containing gas flow.

In a process for the biological oxidation of sulphide, it is important to minimise the undesired production of sulphate and to maximise the desired production of elemental sulphur. It is known that the formation of elemental sulphur over sulphate can be promoted by controlling the oxygen supply.

In WO98/04503 a process is disclosed for the biological treatment of a spent caustic solution comprising sulphides in an aerobic reactor containing sulphur-oxidising bacteria wherein the redox potential in the reactor is controlled. In the process of WO98/04503, the sulphide oxidising reaction is controlled, i.e. elemental sulphur formation is promoted over sulphate formation, by adjusting the redox potential of the medium of oxidation at a value below −300 mV.

Outside the field of bacterial treatment of aqueous solutions, WO01/27042 is specifically concerned with the treatment of process fluids containing solid particles. In WO01/27042 an apparatus is described containing a treatment chamber having at least two interior regions wherein gas bubble inlets and fluid inlet and outlet ducts are arranged such that the process fluid is caused to follow circulating (spiraling) paths in opposite (clockwise vs. anticlockwise) directions along the length of chamber. The circulation-driving bubble inlets are arranged in a plurality of rows so as to create a "curtain" of bubbles between two regions of opposite circulation, such that the process fluid must pass across the curtain of bubbles in its transit through the vessel, whereby any relatively dense solid particles will, on passing through the bubble curtain, experience a significant reduction in buoyancy thereby falling into a solids-collection region arranged between the bubble inlet rows.

There is a need in the art to improve processes for oxidation of sulphide by using sulphide-oxidising bacteria by further controlling the oxidation reaction, in particular to avoid undesired abiotic reactions such as thiosulphate formation due to locally high sulphide concentrations in the reactor.

SUMMARY OF THE INVENTION

It has now been found that the formation of elemental sulphur over the formation of thiosulphate in a process for the oxidation of sulphide by means of sulphide-oxidising bacteria is importantly improved by creating, in a reaction zone containing sulphide-oxidising bacteria in an aqueous reaction medium and not comprising vertically extending separation walls, aerated and non-aerated zones and injecting the sulphide-containing feed stream in a non-aerated zone. It has been found that by thus creating non-aerated and aerated zones that do not need to be separated from each other by means of vertically extending reactor internals, sufficient circulation of aqueous medium occurs to quickly dilute the sulphide concentration that is entering the reactor. Thus, the sulphide concentration in the reaction medium is sufficiently low to minimise undesired thiosulphate formation.

Accordingly, the present invention relates to a process for removing sulphide from an aqueous solution comprising sulphide, wherein the aqueous solution is subjected to sulphide-oxidising bacteria in the presence of oxygen in a reactor to oxidise sulphide to elemental sulphur, the process comprising:

a) providing the aqueous solution comprising sulphide;
b) supplying a molecular-oxygen containing gas to the reactor containing the sulphide-oxidising bacteria in an aqueous medium, such that one or more aerated zones and one or more non-aerated zones are created in the aqueous medium with upward liquid flow in the aerated zones and downward liquid flow in the non-aerated zones;
c) supplying the aqueous solution comprising sulphide to the reactor by injecting the aqueous solution in the one or more non-aerated zones, wherein the one or more aerated zone(s) are not separated from the one or more non-aerated zone(s) by means of vertically extending reactor internals.

In an alternative but equivalent wording, the present invention relates to a process for removing sulphide from an aqueous solution comprising sulphide, wherein the aqueous solution is subjected to sulphide-oxidising bacteria in an aqueous medium in the presence of oxygen in a reactor to oxidise sulphide to elemental sulphur, the process comprising:

a) providing the aqueous solution comprising sulphide;
b) supplying an oxygen-containing gas in a lower section of only a part of the cross-sectional area of the reactor, such that one or more aerated zones and one or more non-aerated zones are created in the aqueous medium, said aerated zones being located above said part in which the oxygen-containing gas is supplied, with upward liquid flow in the aerated zones and downward liquid flow in the non-aerated zones;

c) supplying the aqueous solution comprising sulphide into the one or more non-aerated zones only, at a position that is higher than said lower section.

An advantage of the process according to the invention is that no mixers are needed in order to quickly dilute the inlet stream of aqueous solution with aqueous medium in the reactor. The reactor is operated thus that aqueous medium is circulated as a result of the upward and downward flow created by supplying air or another molecular-oxygen comprising gas to carefully chosen areas of the reaction zone.

It is a unique aspect of the invention that the aqueous solution comprising sulphide is injected into non-aerated zones. The benefits of injection aqueous solution comprising sulphide into such non-aerated zones are that the strong dilution of sulphide prior to entering the aerated zone reduces the production of undesired by-products and enhances sulphur production. Even in prior art systems employing downer pipes to which no air is purposely fed (see e.g. comparative Example 2), it has not been possible to create non-aerated zones for injection of aqueous solution comprising sulphide, as in the present invention.

In the process of the invention, no fixed reactor internals, such as downer pipes or vertical separation walls extending over a major fraction of the vertical height of the reactor, for separating aerated and non-aerated zones, are needed in order to create aerated and non-aerated zones that result in upward and downward flow of reaction medium.

Within the context of the present invention, the term "not separated from the one or more non-aerated zone(s) by means of vertically extending reactor internals" is preferably understood to refer to the absence of means for separating the one or more aerated zone(s) from the one or more non-aerated zone(s), whereby such means vertically extend or are exclusively present in the region of the reactor lying above the height where injection of the aqueous solution comprising sulphide into the reactor takes place. Thus, the process of the invention does preferably not exclude the presence of reactor internals of limited height, such as vertical baffles being positioned in a lower section of the reactor having a height not exceeding the height where injection of the aqueous solution comprising sulphide into the reactor takes place.

If such reactor internals of limited height are present, it is preferred that each of such internal extends over less than 50%, more preferably less than 40%, even more preferably less than 30%, yet even more preferably less than 20%, most preferably less than 10% of the height of the reactor (seen from the lower end of the non-aerated zone).

It has been found that in the process according to the invention, dilution of inlet sulphide is achieved much quicker than in a reactor with vertical separation walls for separating aerated and non-aerated zones.

The process of the invention typically comprises further steps d) of discharging liquid from the reactor and e) separating elemental sulphur and optionally bacterial sludge from the discharged liquid. The liquid is preferably carried off from the upper part of the reactor, e.g. by overflow means at the upper liquid level of the reactor liquid. Preferably such overflow means are located at relatively quiet locations, i.e. adjacent to non-aerated zones, rather than to aerated zones of the reactor. The liquid resulting from separating the elemental sulphur (and possibly bacterial mass) can be further treated, and/or disposed or reused as a process liquid. The elemental sulphur can be valorised as known in the art, e.g. for the production of fertilisers or for the production of sulphuric acid.

The process according to the invention can suitably be applied to remove sulphide from any aqueous solution containing substantial levels of sulphide, either as directly produced as such or as a result of e.g. anaerobic treatment of sulphate and/or sulphite-containing effluents.

The process of the invention is particularly suited for the desulphurization of an aqueous liquid used as an absorbing liquid for removing sulphur compounds, in particular hydrogen sulphide, from a gas stream.

Accordingly, the invention further relates to a process for purifying a gaseous stream comprising sulphur compounds, the process comprising the following steps:
A) contacting the gaseous stream comprising sulphur compounds with an aqueous solution wherein sulphur compounds are dissolved to obtain a purified gaseous stream and an aqueous solution comprising sulphide;
B) removing sulphide from the aqueous solution comprising sulphide obtained in step A) by subjecting the aqueous solution to sulphide-oxidising bacteria in the presence of oxygen in a reactor to oxidise sulphide to elemental sulphur according to the process as hereinbefore defined;
C) separating elemental sulphur from the aqueous solution to obtain a sulphur slurry and separated aqueous solution; and
D) recycling the separated aqueous solution to step A).

In a preferred embodiment of the invention, the process for removing sulphide from an aqueous solution according to the invention is carried out in a novel reactor having a reaction zone without vertical separation walls and comprising means for supplying molecular-oxygen containing gas in a lower section of the reaction zone wherein only part of the cross-sectional area of the reaction zone is provided with such means. Further, there are injection points for sulphide-containing aqueous solution in the reaction zone, at a position that is higher than the lower section and that is above the part of the cross-sectional area not provided with means for supplying molecular-oxygen containing gas.

Accordingly, the invention relates in a further aspect to a reactor for a process for removing sulphide from an aqueous solution comprising sulphide, wherein the aqueous solution is subjected to sulphide-oxidising bacteria in the presence of oxygen to oxidise sulphide to elemental sulphur, the reactor comprising:
a reaction zone without vertical separation walls;
means for supplying molecular-oxygen located in a lower section of the reaction zone, wherein only a part of the cross-sectional area of the lower section of the reaction zone is provided with the means for supplying molecular-oxygen containing gas; and
means for injecting the aqueous solution comprising sulphide into the reaction zone, which are located in a section of the reaction zone above the lower section and at a position above the part of the cross sectional area of the lower section that is not provided with means for supplying molecular-oxygen containing gas.

As explained herein above, a "reaction zone without vertical separation walls" is preferably understood to refer to a reactor having at least no vertical reactor internals for separating aerated from non-aerated zones present in the section of the reaction zone lying above the position of the means for injecting the aqueous solution comprising sulphide into the reaction zone. Preferably, substantially no or no vertical reactor internals for separating aerated from non-aerated zones are present over the entire height of the reaction zone. Thus, if any reactor internals for separating aerated from non-aerated zones are present in the reaction zone, it is preferred that they each extend over less than 50%, more preferably less than 40%, even more preferably less than 30%, yet even more preferably less than 20%, most preferably less than 10% of the height of the reaction zone (seen from the lower end of the non-aerated zone).

DETAILED DESCRIPTION OF THE INVENTION

Figure 1:
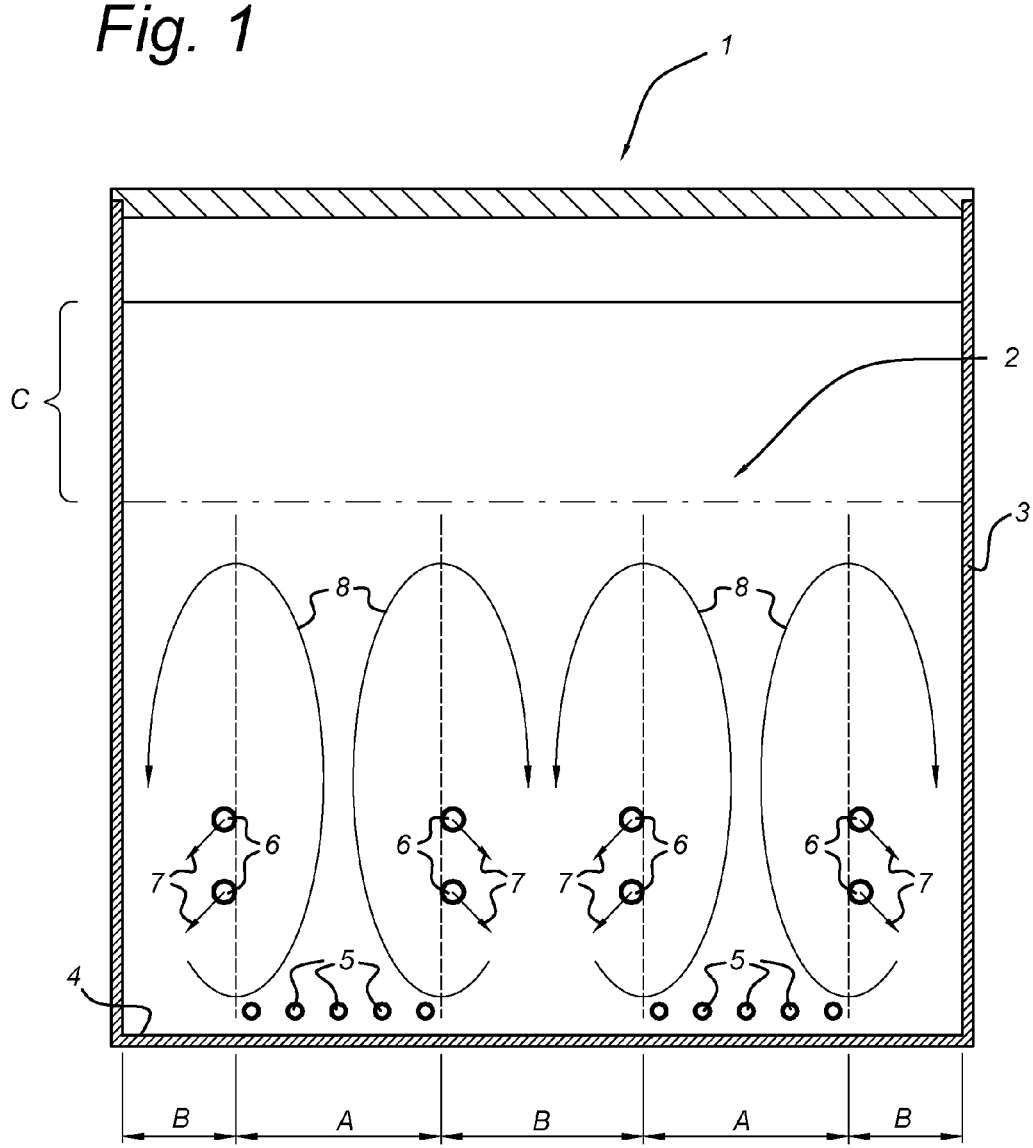
FIG. 1 schematically shows a central longitudinal section of a reactor that can be used in the process according to the invention, showing the configuration of the means for air supply and for supply of the sulphide-comprising aqueous feed stream inside the reactor.

In the process according to the invention an aqueous solution comprising sulphide is subjected to sulphide-oxidising bacteria in the presence of oxygen in a reactor to oxidise sulphide to elemental sulphur.

The reactor contains the sulphide-oxidising bacteria in an aqueous reaction medium, typically the aqueous solution to be treated. The aqueous medium preferably has a pH in the range of from 7 to 10 and may comprises trace compounds, such as for example iron, copper or zinc, as nutrients for the sulphide-oxidising bacteria. A molecular-oxygen containing gas and a feed stream of the aqueous solution are supplied to the reactor. The molecular-oxygen containing gas is supplied to the reactor in such way that one or more aerated zones and one or more non-aerated zones are created in the aqueous medium with upward liquid flow in the aerated zones and downward liquid flow in the non-aerated zones. In the process according to the invention, the one or more aerated zone(s) are not separated from the one or more non-aerated zone(s) by means of vertically extending reactor internals, such as is for example the case in a reactor comprising so-called downers and risers.

Reference herein to aerated zones in the reaction medium is to zones with upward flow of the molecular-oxygen containing gas and, as a result, time-averaged upward flow of the liquid reaction medium. Reference herein to non-aerated zones is to zones without upward flow of molecular-oxygen containing gas and with time-averaged downward flow of liquid reaction medium as a result of the upward liquid flow in the aerated zones.

Creation of such zones in a reactor without vertical separation walls can for example be achieved by carefully choosing the locations of air supply, or of another molecular-oxygen containing gas, to the reactor. In a preferred embodiment, this is achieved by supplying the molecular-oxygen containing gas through means for supplying molecular-oxygen containing gas, such as for example aeration tubes, disks or plates, or diffusers that are located in a lower section of the reactor. The means for supplying molecular-oxygen containing gas are positioned such in the lower section that the molecular-oxygen containing gas is supplied to only a part of the cross-sectional area of the lower section of the reactor. Thus, the upward movement of the gas supplied to the lower section results in an upward liquid flow in a vertical column above the area to which gas is supplied and a downward liquid flow in a vertical column above the area to which no gas is supplied. Aerated and non-aerated areas are thus created in the aqueous medium with upward liquid flow in the aerated zones and downward liquid flow in the non-aerated zones.

It will be appreciated that it is within the skills of the skilled person to carefully choose the locations of air supply to a reactor with a reaction zone without vertical separation walls, in such way that aerated zones with upward liquid flow and non-aerated zones with downward liquid flow are created within the reaction zone. Suitably, the locations of air supply are chosen such that a multitude of alternating aerated zones with upward liquid flow and non-aerated zones with downward liquid flow are created within the reaction zone. In a preferred embodiment, the reactor contains locations of air supply that are arranged such that at least three distinct non-aerated zones with downward liquid flow separated by aerated zones with upward liquid flow are created, the non-aerated zones with downward liquid flow each containing means for injecting aqueous solution comprising sulphide into said non-aerated zone above the lower section.

In the reactor, a zone without time-averaged upward or downward liquid flow and with a concentration of dissolved oxygen that is typically between the dissolved oxygen concentration in the aerated zones and the non-aerated zones, respectively, may occur, for example in an upper layer of reaction medium in the reactor, i.e. above the one or more aerated and non-aerated zones. This will allow liquid medium, including bacteria, to pass from an aerated (upflow) zone to a non-aerated (downflow) zone. Similarly, such a non-upward, non-downward, but predominantly sideward flow zone will occur at the bottom of the reactor allowing liquid medium to pass from a non-aerated (downflow) zone to an aerated (upflow) zone.

The feed stream of the aqueous solution comprising sulphide is supplied to the reactor by injecting the stream into the one or more non-aerated zones. Supply of the sulphide-containing feed stream may be done by any suitable means known in the art, for example by means of one or more injection nozzles. In order to achieve quick dilution of the aqueous solution fed to the reactor with the aqueous medium in the reactor, it is preferred to use more than one points of supply of the aqueous solution, for example by supplying the aqueous solution by means of one of more feed supply tubes located in the non-aerated areas, each tube being provided with injection nozzles.

Preferably, the aqueous solution is injected in the reactor at a height above the height at which the molecular-oxygen containing gas is supplied to the reactor. More preferably, the feed stream is injected at a height that is in the range of 20 to 80%, more preferably of from 25 to 60%, even more preferably of from 30 to 50% of the total height of the non-aerated zone (seen from the lower end of the non-aerated zone). By injecting the aqueous solution at a height in the preferred ranges, use is made of the downward liquid flow in the non-aerated zone(s) for rapid dilution of the sulphide concentration, whilst the feed is injected at a point where the concentration of oxygen is sufficiently low to minimise undesired abiotic oxidation reactions. In an upper section of the non-aerated zone, i.e. at a height above 80% of the height of the non-aerated zone, and to a lesser extent at a height above 60% or 50%, the oxygen concentration is higher due to the presence of gas bubbles entrained with the downward liquid flow in the upper section of the non-aerated zones.

Preferably, the feed stream is injected in the non-aerated zone in a direction away from the nearest aerated zone. Accordingly, the reactor preferably contains means for injecting aqueous solution comprising sulphide arranged such that injection occurs into the reaction zone above the part of the cross-sectional area of the lower section that is not provided with means for supplying molecular-oxygen containing gas and in a direction away from the nearest cross-sectional area of the lower section of the reaction zone that is provided with the means for supplying molecular-oxygen containing gas. Preferably, the means for injecting aqueous solution comprising sulphide is arranged such in the reaction zone that injection of said aqueous solution comprising sulphide occurs in downward direction, i.e. making an angle of at most 85°, preferably at most 60°, more preferably at most 45°, most preferably at most 30° with the vertical plane, in the direction of the non-aerated zone.

It has been found that the process according to the invention can be advantageously applied in a reactor having a relatively small height-to-diameter ratio. Preferably, the reactor has a height-to-diameter ratio below 3.0, more preferably below 2.0, even more preferable in the range of from 0.5 to 1.8. Reference herein to the height of the reactor is to the height of the level of aqueous reaction medium in the reactor, i.e. to the height of the reaction zone.

The reactor may have any suitable shape, preferably the reactor is a vertically extending cylindrical reactor.

The aqueous solution comprising sulphide provided in step a) and supplied to the reactor in step c) may be any aqueous stream comprising sulphide from which sulphide need to be removed. Examples of such streams are loaded washing liquid that has been used for scrubbing a gas stream comprising sulphur compounds and spent caustic solutions.

Reference herein to sulphide is to any form of sulphide, including sulphide anions, mono-hydrogen sulphide ions, hydrogen sulphide, polysulphide, and organic sulphides such as lower alkyl mercaptans and carbon disulphide.

The sulphide concentration in the aqueous solution to be treated is not critical in the process according to the invention. Feed streams with sulphide concentrations (expressed as sulphur) as high as 20 grams per liter or even higher may be used. Preferably, the sulphide concentration in the aqueous solution is in the range of from 10 mg/L to 10 g/L, more preferably of from 20 mg/L to 8 g/L, even more preferably of from 0.1 g/L to 6 g/L, still more preferably of from 0.5 g/L to 3.0 g/L.

In the process according to the invention any suitable sulphide-oxidising bacteria may be used. Suitable sulphide-oxidising bacteria are known in the art. Any sulphide-oxidising bacteria known in the art may be used. Preferably sulphide-oxidising bacteria of the genera *Halothiobacillus, Thioalkalimicrobium, Thioalkalispira, Thioalkalibacter, Thioalkalivibrio* and related bacteria are used. The bacteria may be used as such, or may be supported on a dispersed carrier or may be immobilised on a solid carrier.

The molecular-oxygen comprising gas may be any suitable gas comprising oxygen. Preferably, the molecular-oxygen comprising gas is air or oxygen-depleted air, i.e. air having less than 20% (by volume) of oxygen, e.g. between 2 and 15 vol. % of oxygen. An advantage of using oxygen-depleted air is that the operation of the reactor in terms of gas flow and therewith liquid circulation can be controlled independently of controlling the oxygen concentration in the reactor. Where used herein, the terms "oxygen" and "molecular oxygen" are interchangeable, unless it appears from the context that oxygen is in another chemical form.

The molecular-oxygen containing gas is preferably supplied to the reactor in such amount that an optimum amount of oxygen reactant is present for the required oxidation reaction (sufficient for the oxidation to sulphur; not too much in order to avoid sulphate formation) and that sufficient mixing of feed stream with aqueous medium takes place in order to quickly dilute the inlet sulphide concentration. Preferably, the molecular-oxygen containing gas is supplied at a normal superficial velocity in the range of from 0.25 to 8 cm/s, more preferably of from 0.8 to 4 cm/s. Reference herein to normal superficial velocity is to the superficial velocity at conditions of standard temperature and pressure, i.e. at 0° C. and 1 bar (absolute).

The sulphide-oxidising reaction in the reactor is preferably carried out at a temperature in the range of from 20 to 45° C.

The invention further relates to a process for purifying a gaseous stream comprising sulphur compounds, the process comprising the following steps:

A) contacting the gaseous stream comprising sulphur compounds with an aqueous solution wherein sulphur compounds are dissolved to obtain a purified gaseous stream and an aqueous solution comprising sulphide;

B) removing sulphide from the aqueous solution comprising sulphide obtained in step A) by subjecting the aqueous solution to sulphide-oxidising bacteria in the presence of oxygen in a reactor to oxidise sulphide to elemental sulphur according to the process for removing sulphur from an aqueous solution comprising sulphide according to the invention;

C) separating elemental sulphur from the aqueous solution to obtain a sulphur slurry and separated aqueous solution; and D) recycling the separated aqueous solution to step A).

Step A) is a step for washing a gaseous stream comprising sulphur compounds such as hydrogen sulphide, with an aqueous solution wherein sulphur compounds are dissolved. Such scrubbing or washing steps are well-known in the art, for example from WO 92/10270. The aqueous solution may be any aqueous solution known in the art for this purpose. Examples of preferred solutions are carbonate, bicarbonate or phosphate solutions, more preferably carbonate solutions. Potassium or sodium carbonate solutions are particularly preferred, more in particular sodium carbonate. The aqueous solution used in step a) is preferably a buffered solution with a pH in the range of from 7 to 9.

In step A), a purified gaseous stream and an aqueous solution comprising sulphide are obtained. The aqueous solution comprising sulphide is subjected in step B) to sulphide-oxidising bacteria in the presence of oxygen in a reactor to oxidise sulphide to elemental sulphur as has been described in more detail hereinbefore.

In sulphur recovery step C), the elemental sulphur formed in step B) is separated from the aqueous solution. This may be done by any means known in the art, such as for example by means of sedimentation or other means for solid-liquid separation known in the art. Aqueous solution separated from elemental sulphur in step C) is recycled to scrubbing step A), wherein it is used again for dissolving sulphur compounds.

The gaseous stream to be purified in the process according to the invention may be any gaseous stream comprising hydrogen sulphide or other reduced sulphur compounds such as lower alkyl mercaptans or carbonyl sulphide. Examples of such gaseous streams include biogas, sour natural gas or synthesis gas.

The invention further relates to a reactor that can suitably be used in the process for removal of sulphide from an aqueous solution according to the invention. The reactor comprises:

a reaction zone without (major) vertical separation walls;

means for supplying molecular-oxygen located in a lower section of the reaction zone, wherein only a part of the cross-sectional area of the lower section of the reaction zone is provided with the means for supplying molecular-oxygen containing gas; and means for injecting the aqueous solution comprising sulphide into the reaction zone, which are located in a section of the reaction zone above the lower section and at a position above the part of the cross sectional area of the lower section that is not provided with means for supplying molecular-oxygen containing gas.

The means for supplying molecular-oxygen containing gas in the reactor according to the invention preferably is a grid of aeration tubes, wherein the grid is located in a lower section of the reaction zone and the grid is only covering part of the cross-sectional area of the reaction zone. Thus, oxygen-containing gas is supplied to the lower part of the reaction zone and only to a part of the cross-sectional area of that lower part, such that aerated and non-aerated zones are created during normal operation of the reactor. Preferably, multiple alternating aerated and non-aerated zones are created during normal operation of the reactor. Suitably, the means for supplying molecular-oxygen in the lower section of the reaction zone are located such that at least two aerated zones are created with upward liquid flow in vertical columns above the gas supply means and at least two non-aerated zones are created, wherein injection of aqueous solution comprising sulphide and downward liquid flow in vertical columns above the part of the cross-sectional area without air supply in the lower section occurs.

As explained herein above, a "reaction zone without vertical separation walls" is preferably understood to refer to a reactor having at least no vertical reactor internals for separating aerated from non-aerated zones present in the section of the reaction zone lying above the position of the means for injecting the aqueous solution comprising sulphide into the reaction zone. Preferably, substantially no or no vertical reactor internals between the aerated zones with upward liquid flow in vertical columns above the gas supply means and the non-aerated zones with downward liquid flow in vertical columns above the part of the cross-sectional area without air supply, over the entire height of the reaction zone. Thus, if any reactor internals for separating aerated from non-aerated zones are present in the reaction zone, it is preferred that they each extend over less than 50%, more preferably less than 40%, even more preferably less than 30%, yet even more preferably less than 20%, most preferably less than 10% of the height of the reaction zone (seen from the lower end of the non-aerated zone).

Preferably, the grid of aeration tubes covering only part of the cross-sectional area of the reaction zone comprises first regions of grouped aeration tubes and second regions devoid of aeration tubes wherein the first regions and second regions are alternatingly distributed over the grid. In a preferred embodiment, the grid of aeration tubes comprises at least two regions of horizontally aligned aeration tubes, each region comprising at least two horizontally aligned aeration tubes, said at least two regions of horizontally aligned aeration tubes being interspersed with regions devoid of aeration tubes.

In an alternative preferred embodiment, the grid of aeration tubes comprises at least two regions of aeration tubes, said aeration tubes entering the reactor in a lower section of the reaction zone, following the curvature of the cylindrical outer wall of the reactor and exiting the reactor at a side opposite of the entry side, each region comprising at least two aeration tubes, and said at least two regions of aeration tubes being interspersed with regions devoid of aeration tubes.

The reactor has a reactor height and a reactor diameter and preferably the height to diameter ratio of the reactor is below 3.0, more preferably below 2.0, and preferably the ratio is above 0.3, more preferably above 0.4; even more preferably the ratio is in the range of from 0.5 to 1.8, most preferably from 0.75 to 1.5. The reactor height and diameter can vary broadly, depending primarily on the required capacity. For example, the reactor height can be between 1.5 and 20 m and the reactor diameter can be between 2 and 25 m.

The invention is further illustrated by means of the following, non-limiting drawings.

DETAILED DESCRIPTION OF THE DRAWINGS

FIG. 1 schematically shows a central longitudinal section of a reactor that can be used in the process according to the invention, showing the configuration of the means for air supply and for supply of the sulphide-comprising aqueous solution in the reactor.

Reactor 1 contains aqueous reaction medium 2 in a reaction zone defined by reactor wall 3 and bottom 4. The reaction zone has no vertical separation walls. Air supply tubes 5 are located in the reaction zone near the bottom of the reactor, i.e. in a lower section of the reactor. Air supply tubes 5 are positioned such that only a part the cross-sectional area of the lower section of the reactor is provided with air supply tubes. Air supply tubes 5 each comprise air inlet openings (not shown) over the entire length of the tubes. Thus, air is supplied to the reactor to only a part of the cross-sectional area of its lower section. During normal operation of the reactor, two aerated zones A with upward liquid flow are created in vertical columns above air supply lines 5 and three non-aerated zones B are created in vertical columns above the part of the cross-sectional area without air supply lines in the lower section (one in the centre of the reactor and at the sides of the reactor between reactor wall 3 and the aerated zones A). Reactor 1 is further provided with inlet tubes 6 for supplying a sulphide-comprising aqueous solution to reactor 1. Feed inlet tubes 6 are located in the non-aerated zones B at a height above the air supply tubes 5. The aqueous solution is injected into the non-aerated zones B in a direction away of the nearest aerated zone. Arrows 7 show the direction of injection of the feed aqueous solution into reactor 1. The liquid circulation in aqueous medium 2 reactor is shown with arrow 8. In aerated zones A upward flow of liquid occurs and in non-aerated zones B, downward flow of liquid occurs. Above aerated zones A and non-aerated zones B, there is a zone C in aqueous medium 2 wherein no time-averaged upward or downward flow occurs. The reactor will be further provided with a gas outlet at the top of the reactor (not shown) and with a liquid outlet, e.g. as an overflow at the upper liquid level of the reactor (not shown).

Figure 2A:
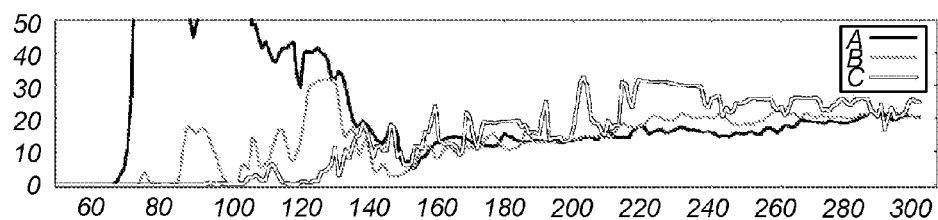
In FIGS. 2a, 2b, and 2c is shown the sulphide concentration as a function of time at three different heights in the reactor for simulation experiments 1 (comparative), 2 (comparative), and 3 (according to the invention).
Figure 2B:
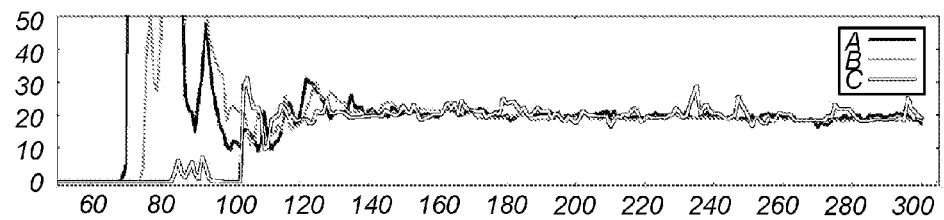
Figure 2C:
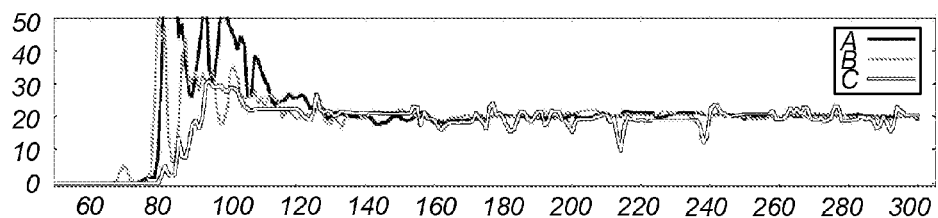

FIGS. 2a, 2b, and 2c show the sulphide concentration as a function of time at three different heights in the reactor for simulation experiments 1 (comparative), 2 (comparative), and 3 (according to the invention) described herein below.

EXAMPLES

In order to compare the process according to the invention with a process using a conventional bioreactor (no creation of aerated and non-aerated zones in the aqueous reaction medium) and with a process wherein aerated and non-aerated zones are created which are separated from each other by means of vertical separation walls (a reactor with so-called downers for downward flow of reaction medium), simulation calculations using computational fluid dynamics were made.

Experiment 1

Comparative

In a first comparative simulation, the sulphide concentration as a function of time in a conventional vertically extending cylindrical bioreactor (reactor 1) was calculated at three different heights (at 11%, 44% and 88% of the height of the reaction liquid in the reactor, seen from the reactor bottom). The height to diameter ratio of the reactor was 0.95.

In the simulation experiment, both air and sulphide-containing aqueous solution are fed to the lower section of the reactor and both are evenly supplied over the entire cross-sectional area of the reactor, each via a grid of inlet tubes positioned at the bottom of the reaction zone. The superficial air velocity is 1.8 normal cm/s. The assumed air bubble diameter is 10 mm. After an initial period of 60 seconds, a pulse of an aqueous solution with sulphide is given in such amount that the final equilibrium concentration of sulphide in the aqueous medium is 20 mg/l.

Experiment 2

Comparative

Simulation experiment 1 was repeated for a reactor with the same dimensions (vertically extending cylindrical reactor with a height to diameter ratio of 0.95), but now with five downer pipes evenly distributed over the cross-sectional area of the reactor. The total downer cross-sectional area is 12.5% of the reactor cross-sectional area. The height of the downers is 50% of the reactor height and the lower ends of the downers are positioned at a distance equal to 50% of the downer diameter from the reactor bottom. Air is fed to the reaction zone via a grid of aeration tubes positioned at the bottom of the reaction zone. No air was fed to the reaction zone directly underneath the downer pipes.

The superficial air velocity is 1.8 normal cm/s. The assumed air bubble diameter is 10 mm. After an initial period of 60 seconds, an aqueous solution with sulphide is pulsed to each of the downers near the upper end of each downer in such amount that the final equilibrium concentration of sulphide in the aqueous medium is 20 mg/l.

Experiment 3

According to the Invention

Simulation experiment 1 was repeated for a reactor with the same dimensions (vertically extending cylindrical reactor with a height to diameter ratio of 0.95), but now with air only supplied to 50% of the cross sectional area of the reaction zone in a configuration as shown in FIG. 1, i.e. air is supplied to two different areas of the reactor bottom. The superficial air velocity is 1.8 normal cm/s. The assumed air bubble diameter is 10 mm. After an initial period of 60 seconds, an aqueous solution with sulphide is pulsed to at two height levels (at 18% and 28% of the height of the reaction zone seen from the reactor bottom) in each of the non-aerated zones, i.e. in the vertical columns above the parts of the cross-sectional area of the reactor not provided with air (zones B as shown in FIG. 1), in such amount that the final equilibrium concentration of sulphide in the aqueous medium is 20 mg/l.

For each of experiments 1, 2 and 3, the liquid velocities and local gas hold-up were simulated in time and the sulphide concentrations as a function of time, at three different heights (at 11%, 44% and 88% of the reactor height seen from the bottom) on the central longitudinal axis of the reactor, were calculated. The results are shown in FIGS. 2a, 2b and 2c for experiments 1, 2 and 3, respectively. In FIGS. 2a, 2b and 2b, the sulphide concentration (in mg/liter) is given as a function of time (in seconds). Lines A, B, and C give the sulphide concentration at a height of 11%, 44% and 88%, respectively.

It can be seen that the dilution time, i.e. the time needed for achieving the equilibrium concentration of sulphide across the reactor, is 2.3 times shorter in the process according to the invention (experiment 3) than in a process using a conventional bioreactor (experiment 1). Compared to a process using a reactor with downers (experiment 2), i.e. with vertical separation walls inside the reaction zone, the dilution time is 10% shorter.

The invention claimed is:

1. A process for removing sulfide from an aqueous solution comprising sulfide, in a vertically extending reactor, the process comprising:
   (a) providing the aqueous solution comprising sulfide;
   (b) supplying a molecular-oxygen containing gas to the reactor containing sulfide-oxidising bacteria in an aqueous medium, such that multiple vertical aerated zones and multiple vertical non-aerated zones are created in the aqueous medium with upward liquid flow in the aerated zones and downward liquid flow in the non-aerated zones;
   (c) supplying a feed stream of the aqueous solution comprising sulfide to the reactor by injecting the feed stream in the non-aerated zones;
   (d) subjecting the solution comprising sulfide to sulfide-oxidising bacteria provided in the reactor to oxidize sulfide to elemental sulfur:
   (e) discharging liquid from the reactor: and
   (f) separating elemental sulfur from the discharged liquid: wherein the aerated zones are not separated from the zones by means of vertically extending reactor internals.

2. The process according to claim 1, wherein the aerated zones and the non-aerated zones are created by supplying the molecular-oxygen containing gas through means for supplying molecular-oxygen containing gas located in a lower section of the reactor, wherein the molecular-oxygen containing gas is supplied to only a part of the cross-sectional area of the lower section of the reactor.

3. The process according to claim 2, wherein the means for supplying molecular-oxygen containing gas comprise aeration tubes.

4. The process according to claim 1, wherein the aqueous solution comprising sulfide is injected into the non-aerated zones at a height above the height at which the molecular-oxygen containing gas is supplied to the reactor.

5. The process according to claim 4, wherein the aqueous solution comprising sulfide is injected into the non-aerated zones in a direction away from the nearest aerated zone.

6. The process according to claim 1, wherein the molecular-oxygen containing gas is air or oxygen-depleted air.

7. The process according to claim 1, wherein the aqueous solution has a sulfide concentration in the range of from 0.1 g/L to 6 g/L.

8. The process according to claim 1, wherein the reactor has a reactor height and a reactor diameter and wherein the height to diameter ratio of the reactor is in the range of from 0.5 to 1.8.

9. The process according to claim 1, wherein the molecular-oxygen containing gas is supplied to the reactor at a normal superficial velocity in the range of from 0.8 to 4 cm/s.

10. A process for purifying a gaseous stream comprising sulfur compounds, the process comprising the following steps:
(A) contacting the gaseous stream comprising sulfur compounds with an aqueous solution wherein sulfur compounds are dissolved to obtain a purified gaseous stream and an aqueous solution comprising sulfide;
(B) removing sulfide from the aqueous solution comprising sulfide obtained in step A) in a reactor containing sulfide-oxidising bacteria in an aqueous medium comprising one or more upward flowing aerated zones and one or more downward-flowing non-aerated zones, by injecting the aqueous solution comprising sulfide into the one or more the non-aerated zones, wherein the aerated zones are not separated from the non-aerated zones by means of vertically extending reactor internals;
(C) separating elemental sulfur from the aqueous solution to obtain a sulfur slurry and separated aqueous solution; and
(D) recycling the separated aqueous solution to step A).

11. A process for removing sulfide from an aqueous solution comprising sulfide, in a vertically extending reactor containing sulfide-oxidising bacteria in an aqueous medium, the process comprising:
(a) providing a feed stream of the aqueous solution comprising sulfide;
(b) aerating a part of the cross-sectional area in a lower section of the reactor, such that multiple vertical aerated zones are created in the aqueous medium above the aerated part and non-aerated zones are created in the aqueous medium above the multiple vertical non-aerated part, with upward liquid flow in the aerated zones and downward liquid flow in the non-aerated zones;
(c) injecting the feed stream into the non-aerated zones above the height at which the reactor is aerated, in a downward direction away from the nearest aerated zone;
(d) subjecting the solution comprising sulfide to the sulfide-oxidising bacteria to oxidize sulfide to elemental sulfur;
(e) discharging liquid from the reactor; and
(f) separating elemental sulfur from the discharged liquid.

12. The process according to claim 11, wherein the aqueous solution has a sulfide concentration in the range of from 0.1 g/L to 6 g/L.

13. The process according to claim 11, wherein the aerated part is aerated with a gas containing 2-15% of oxygen.

14. The process according to claim 11, wherein the feed stream is injected at a height that is in the range of 25 to 60%, of the total height of the non-aerated zone.

15. A process for purifying a gaseous stream comprising sulfur compounds, comprising the following steps:
(A) contacting the gaseous stream comprising sulfur compounds with an aqueous solution having a pH between 7 and 10, to obtain a purified gaseous stream and an aqueous solution comprising sulfide;
(B) removing sulfide from the aqueous solution comprising sulfide obtained in step A) in a reactor containing sulfide-oxidising bacteria in an aqueous medium comprising one or more upward flowing aerated zones and one or more downward-flowing non-aerated zones, by injecting the aqueous solution comprising sulfide into one or more of the non-aerated zones above the height at which the reactor is aerated, in a downward direction away from the nearest aerated zone;
(C) separating elemental sulfur from the aqueous solution to obtain a sulfur slurry and separated aqueous solution; and
(D) recycling the separated aqueous solution to step A).

16. The process of claim 1, wherein the aqueous solution comprising sulfide is provided by contacting a gaseous stream comprising sulfur compounds with an aqueous washing solution to obtain a purified gaseous stream and the aqueous solution comprising sulfide, the process further comprising recycling the liquid from which elemental sulfur has been separated in step e) as the aqueous washing solution.

17. The process of claim 11, wherein the aqueous solution comprising sulfide is provided by contacting a gaseous stream comprising sulfur compounds with an aqueous washing solution to obtain a purified gaseous stream and the aqueous solution comprising sulfide, the process further comprising recycling the liquid from which elemental sulfur has been separated in step e) as the aqueous washing solution.

* * * * *